(12) United States Patent
Poust et al.

(10) Patent No.: US 11,098,279 B2
(45) Date of Patent: Aug. 24, 2021

(54) LIQUID BASED SELECTION AND CELL ISOLATION

(71) Applicant: Zymergen Inc., Emeryville, CA (US)

(72) Inventors: Sean Poust, El Cerrito, CA (US); Vytas SunSpiral, Oakland, CA (US); William Serber, Oakland, CA (US); Matthew Jonathan Myers, Oakland, CA (US); Sara da Luz Areosa Cleto, Emeryville, CA (US); Philip Weyman, Alameda, CA (US)

(73) Assignee: ZYMERGEN INC., Emeryville, CA (US)

( * ) Notice: Subject to any disclaimer, the term of this patent is extended or adjusted under 35 U.S.C. 154(b) by 0 days.

(21) Appl. No.: 16/460,455

(22) Filed: Jul. 2, 2019

(65) Prior Publication Data
US 2020/0032356 A1 Jan. 30, 2020

Related U.S. Application Data

(60) Provisional application No. 62/693,738, filed on Jul. 3, 2018.

(51) Int. Cl.
*C12N 1/20* (2006.01)
*C12N 15/74* (2006.01)
*C12R 1/01* (2006.01)

(52) U.S. Cl.
CPC .............. *C12N 1/205* (2021.05); *C12N 1/20* (2013.01); *C12N 15/74* (2013.01); *C12R 2001/01* (2021.05)

(58) Field of Classification Search
None
See application file for complete search history.

(56) References Cited

U.S. PATENT DOCUMENTS

2017/0159045 A1 6/2017 Serber et al.

OTHER PUBLICATIONS

Gross et al. Technologies for Single-Cell Isolation. Aug. 2015. International Journal of Molecular Science. vol. 16, No. 8, pp. 16897-16919. (Year: 2015).*
Kato et al. Unprecedented Cell-Selection Using Ultra-Quick Freezing Combined with Aquaporin Expression. Feb. 18, 2014. PLOS ONE. vol. 9, Issue 2, e87644, pp. 1-10. (Year: 2014).*
Peters et al. Enrichment of Mutants of Mucor racemosus by Differential Freeze-killing. Journal of General Microbiology. 1978. vol. 105, pp. 77-81. (Year: 1978).*
Reyrat, Jean-Marc, et al., "Counterselectable Markers: Untapped Tools for Bacterial Genetics and Pathogenesis," *Infect Immun*, Sep. 1998, 66(9), pp. 4011-4017.
Konczal, Jennifer, et al., "Streamlining workflow and automation to accelerate laboratory scale protein production," Protein Expression and Purification, 133, 2017, pp. 160-169.
International Search Report and Written Opinion dated Sep. 20, 2019, issued in PCT Application No. PCT/US19/40320.
Riba, J., et al., "Label-free isolation and deposition of single bacterial cells from heterogeneous samples for clonal culturing," Scientific Reports, 6:32837, DOI: 10.1038/srep32837, Published Sep. 6, 2016, pp. 1-9.

* cited by examiner

*Primary Examiner* — Channing S Mahatan
(74) *Attorney, Agent, or Firm* — Weaver Austin Villeneuve & Sampson LLP

(57) ABSTRACT

Aspects of this disclosure relate to liquid-based workflows for strain engineering. In strain engineering, cells undergo a modification process to acquire a desired change or changes in the cells. Some of the cells accept the change or changes and some do not. Provided herein are liquid-based methods for selecting the population of cells that have accepted the change or changes. Also provided herein are liquid-based methods for removing markers from transformed cells and liquid-based methods for isolating clonally pure populations of cells.

29 Claims, 16 Drawing Sheets

LIQUID BASED SELECTION AND CELL ISOLATION

CROSS-REFERENCE TO RELATED APPLICATIONS

This application claims benefit of and priority to US Provisional Application No. 62/693,738, filed on Jul. 3, 2018, which is incorporated herein by reference in its entirety for all purposes.

FIELD

This disclosure pertains to workflows for microbial strain engineering. More particularly, it pertains to liquid-based workflows that reduce or eliminate plating on a solid medium.

BACKGROUND

Microbial strain engineering involves cell editing processes, such as transformation, that produce mixed populations of cells including cells that include one or more desired changes and those that do not. Following a transformation or other editing processes, cells may be plated on a solid growth medium that contains a solidifying agent such as agar, that includes a selection or counter-selection additive that kills cells that do not include the desired change or changes. The cells are grown until distinct colonies appear and are picked manually or using a colony picking machine, so that they can be collected, genotyped and stored. Plating on, and sampling from, solid media is cumbersome and time consuming, with plating taking hours and colony growth taking days in some instances. Further, agar media is prone to contamination, requires pouring into plates, manual picking is tedious and colony picking machines are often weak points in automated strain engineering workflows, introducing errors or failures.

It would be desirable to decrease the time to perform strain engineering. It would further be desirable to reduce or eliminate agar-based steps and colony picking.

SUMMARY

This disclosure presents methods for isolating clonally pure samples of genetically altered micro-organisms in liquid. The methods involve selection and/or counter-selection in liquid media. The methods involve liquid-based cell selection and isolation of clonally pure populations. A process including one or more of selection, counter-selection, and isolation may be performed without plating on a solid medium.

One aspect of the disclosure relates to a method including providing a mixed population of cells, the mixed population including first mutant cells and non-mutant cells, the first mutant cells having a target DNA sequence integrated on a left or right homology arm, a selection marker, and a counter-selection marker integrated into their genomes, the selection marker coding for resistance to a selection agent and the counter-selection marker coding for one or more proteins that lead to cell death in counter-selective conditions; in liquid, enriching the first mutant cells relative to the non-mutant cells in the mixed population to produce a homogenous population of first mutant cells; and in liquid, removing the selection marker and the counter-selection marker from some cells of the population enriched for the first mutant cells.

In some embodiments, the method is performed without generating clonal populations on a plate containing solid growth medium and selection or counter-selection additives. In some embodiments, the method further includes performing a transformation process to produce the mixed population. In some such embodiments, the method further includes after performing the transformation process, adding a liquid medium including the selection agent to the mixed population to select the first mutant cells.

In some embodiments, the non-mutant cells include persister cells, the persister cells being metabolically inactive cells. In some such embodiments, enriching the first mutant cells relative to the persister cells includes adding a cryoprotectant and then freezing and thawing the mixed population.

In some embodiments, the non-mutant cells include cells that spontaneously develop resistance to the selection agent but do not have the target DNA sequence. In some such embodiments, enriching the first mutant cells relative to the cells that spontaneously develop resistance to the selection agent but do not have the target DNA sequence includes freezing and thawing the mixed population.

In some embodiments, the non-mutant cells include plasmid-based persister cells that carry a non-integrated plasmid including the selection marker and are resistant to the selection agent but that cannot increase in number. In some such embodiments, enriching the first mutant cells relative to the plasmid based-persister cells includes diluting and outgrowing the mixed population cells.

In some embodiments, enriching the first mutant cells relative to the non-mutant cells in the mixed population includes freezing and thawing the mixed population. In some such embodiments, freezing and thawing is performed after operations of post-transformation cell recovery and adding a liquid medium including the selection agent to the mixed population.

In some embodiments, enriching the first mutant cells relative to the non-mutant cells from the mixed population includes diluting and outgrowing the mixed population cells after thawing. In some embodiments, removing the selection marker and counter-selection marker from cells of the population enriched for the first mutant cells includes producing a second mixed population, the second mixed population including first mutant cells, second mutant cells having the target DNA sequence without the selection marker and counter-selection marker integrated into their genomes, and base strain cells.

In some embodiments, the method further includes isolating the cells of the second mixed population. In some such embodiments, isolating the cells of the second mixed population includes optical identification of individual cells. In some such embodiments, isolating the cells further includes single cell dispensing of the optically identified individual cells. In some such embodiments, isolating the cells includes sorting with one or more of the group consisting of a viability stain, a fluorescent protein, and a reporting reagent.

In some embodiments, the method further includes isolating the cells of the enriched population through a limiting dilution process. In some embodiments, the method further includes performing a limiting dilution of the enriched population into a plurality of wells containing a counter-selection agent such that substantially all of the wells contain no more than one cell that survives counter-selection.

In some embodiments, the cells are selected from: bacterial cells and fungal cells. In some embodiments, the cells are gram-negative bacterial cells.

Another aspect of the disclosure relates to method including: providing a mixed population of cells, the mixed population including first mutant cells and non-mutant cells, the first mutant cells having a target DNA sequence integrated on a left or right homology arm, a selection marker, and a counter-selection marker integrated into their genomes, the selection marker coding for resistance to a selection agent; and in liquid, enriching the first mutant cells relative to the non-mutant cells in the mixed population to produce a homogenous population of the first mutant cells.

In some embodiments, the method is performed without generating clonal populations on a plate containing a solid growth medium and the selection agent. In some embodiments, the non-mutant cells include plasmid-based persister cells that that carry a non-integrated plasmid including the selection marker and are resistant to the selection agent but that cannot increase in number. In some embodiments, the non-mutant cells include cells that spontaneously develop resistance to the selection agent but do not have the target DNA sequence.

In some embodiments, enriching the first mutant cells relative to the cells that spontaneously develop resistance to the selection agent but do not have the target DNA sequence includes freezing and thawing the mixed population. In some embodiments, the non-mutant cells include plasmid-based persister cells that carry a non-integrated plasmid including the selection marker and are resistant to the selection agent but that cannot increase in number. In some embodiments, enriching the first mutant cells relative to the plasmid-based persister cells includes diluting and outgrowing the mixed population cells.

In some embodiments, enriching the first mutant cells relative to the non-mutant cells in the mixed population includes freezing and thawing the mixed population. In some such embodiments, the freezing and thawing is performed immediately after post-transformation cell recovery and adding a liquid medium including the selection agent to the mixed population.

In some embodiments, enriching the first mutant cells relative to the non-mutant cells includes, after thawing, a first dilution and outgrowth of the mixed population cells in a liquid medium containing the selection agent. In some embodiments, enriching the first mutant cells relative to the non-mutant cells includes a second dilution and outgrowth of the mixed population cells in the liquid medium containing the selection agent.

In some embodiments, the cells are selected from: bacterial cells and fungal cells. In some embodiments, the cells are gram-negative bacterial cells.

Another aspect of the disclosure relates to a method including: receiving, in liquid, a substantially homogenous population of first mutant cells having a target DNA sequence and one or more counter-selection markers integrated into their genomes, the one or more counter-selection markers coding for one or more proteins that lead to cell death in counter-selective conditions; in liquid, culturing the substantially homogenous population of first mutant cells in counter-selective conditions to produce second mutant cells having the target DNA sequence without the counter-selection marker integrated into their genomes; and in liquid, producing clonally isolated populations of the second mutant cells.

In some embodiments, method is performed without generating clonal populations on a plate containing solid growth medium and a counter-selection agent. In some embodiments, the method further includes producing a second mixed population, the second mixed population including second mutant cells and base strain cells. In some embodiments, the method further includes optical identification of individual second mutant cells. In some such embodiments, producing clonally isolated populations of the second mutant cells includes single cell dispensing of the optically identified individual cells.

In some embodiments, producing clonally isolated populations includes sorting with one or more of the group consisting of a viability stain, a fluorescent protein, and a reporting reagent. In some embodiments, the method further includes performing a limiting dilution of the first homogenous population into a plurality of wells containing a counter-selection agent such that substantially all of the wells contain no more than one cell that survives counter-selection.

In some embodiments, the cells are selected from: bacterial cells and fungal cells. In some embodiments, the cells are gram-negative bacterial cells.

Another aspect of the disclosure relates to a method including (a) providing a population of cells including transformant cells and nontransformant cells, the transformant cells including a selection marker; (b) culturing the population of cells in a liquid medium that selects for the selection marker; and (c) in liquid, providing a plurality of clonally pure populations of cells.

In some embodiments, the method is performed without generating clonal populations on a plate containing solid growth medium and a selection additive. In some embodiments, (c) includes, in liquid, isolating cells of the cell population to provide a plurality of isolated single cell populations. In some embodiments, (c) further includes culturing the isolated cells in a liquid medium to provide the plurality of clonally pure populations of cells.

In some embodiments, isolating cells includes a limiting dilution process. In some embodiments, the method further includes genotyping the clonally pure populations of cells. In some embodiments, the method further includes optical identification of individual cells. In some embodiments, providing a plurality of single cell populations includes single cell dispensing of the optically identified individual cells. In some embodiments, providing a plurality of isolated single cells populations includes sorting with one or more of the group consisting of a viability stain, a fluorescent protein, and a reporting reagent.

These and other features of the disclosure will be presented below with reference to the associated drawings.

DETAILED DESCRIPTION

Terminology

Figure 1:
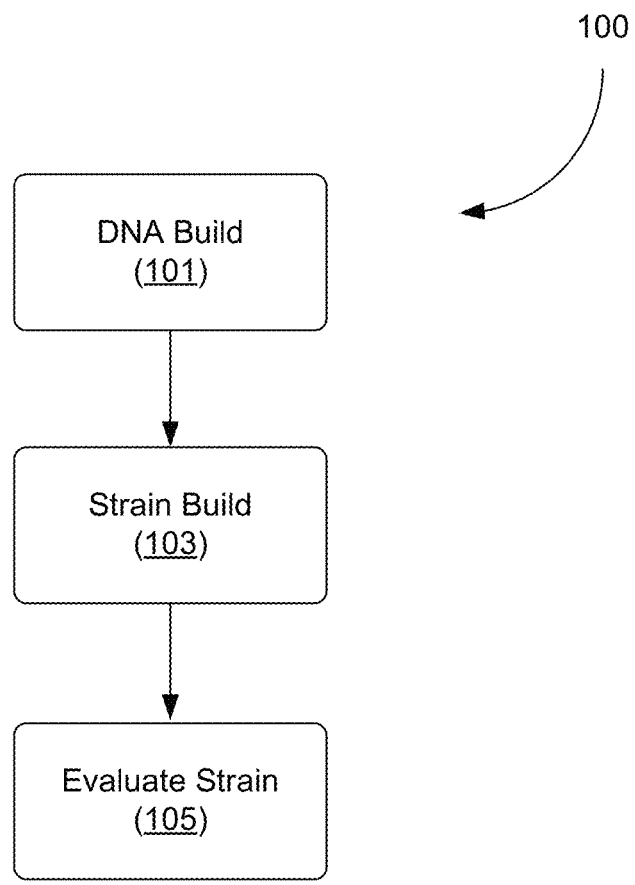
FIG. 1 is a flowchart depicting of a high-level process for high throughput strain engineering.

Terms used in the claims and specification are defined as set forth below unless otherwise specified.

The term "base strain" refers to the starting strain prior to insertion of the current round of genetic changes.

The term "mutant" with reference to cells refers to cells that are genetically different from the initial base strain cells.

The terms "clonally pure population" or "isogenic population" refer to a cell population that contains genetically identical cells or cells that are genetically identical but for a targeted genetic change.

The term "homogenous population" with respect to mutant cells refers to a cell population where the live cells all express the same mutant phenotype relative to the cellular population from which the mutant cells are derived. The expression of the mutant phenotype in the mutant cells of the homogenous population may result from the incorporation of a vector having a target DNA sequence into each cell's genome.

The terms "loop-in" or "looping-in" refer to the process of integrating extraneous DNA into the genomes of microbial cells via a single recombination event and the resulting microbial cells. The extraneous DNA may include one or more target DNA sequences, one or more markers, and right and left homology sequences.

The terms "loop-out" or "looping-out" refer to the process of excising part of the extraneous DNA previously integrated into the genomes of microbial cells and the resulting microbial cells. This may be done via a second DNA recombination step. A loop-out cell is a mutant cell that includes a desired mutation but none of the remaining extraneous DNA sequences, such as selection and counter-selection markers or other functional and structural DNA portions of the vector.

Introduction

Aspects of this disclosure relate to exclusively liquid-based workflows for strain engineering. In strain engineering, cells undergo a modification process to acquire one or more desired changes in their DNA. Some of the cells incorporate the change or changes, and some do not. Provided herein are liquid-based methods for selecting the population of cells that have accepted the change or changes, and eliminate those that have not. Also provided herein are liquid-based methods to select for cells that have gone through an additional recombination step that led to the removal of markers from their chromosome. Also provided herein are liquid-based methods for isolating clonally pure populations of cells.

Aspects of the disclosure include liquid-based workflows for selecting and/or isolating cells that include episomal DNA segments. In some embodiments, the DNA segments are vectors capable of inserting desired target DNA sections into the chromosome of a host organism, via DNA with the same sequence. The vectors may include, for example, the target DNA and homology arms (same DNA sequences) as well as one or more markers. The liquid-based workflows may be part of a process (referred to as "DNA build") that generates and clones DNA plasmids or other vectors for integration into a host strain. The liquid-based workflows may include selection in liquid media, and in some implementations, may further include isolation of clonally pure populations in liquid. The liquid based workflows may be performed without plating on a solid media that includes a selection or counter-selection agent or agents.

Aspects of the disclosure include liquid-based workflows for selecting mutant cells that have a target DNA sequence of interest and additional plasmid DNA integrated into their genomes (also referred to as loop-in cells), and generating homogenous populations of the mutant cells. Further aspects include liquid-based workflows for excising markers and additional plasmid DNA from mutant cells (also referred to as looping-out), and isolating clonally pure populations of the loop-out cells.

In some implementations, the methods may be implemented as part of a high throughput method for strain engineering. An example of a high throughput method for strain engineering is provided in FIG. 1. In FIG. 1, a flowchart represented by reference number 100 begins with an operation 101 referred to as "DNA Build." In DNA Build, DNA to be integrated into a host strain is assembled and cloned into a transformation plasmid or other vector. Liquid-based workflows that may be implemented in the context of DNA Build are described below with respect to FIGS. 15 and 16.

Next, an operation referred to as "Strain Build" is performed in an operation 103. In Strain Build, the DNA built in operation 101 is moved into the genome of a host strain, where the mutation(s) are to be introduced. In some implementations, this includes transforming the DNA assembled in operation 101 into host cells, utilizing any transformation method such as, but not limited to, electroporation, conjugation and phage transduction. A target DNA sequence is integrated into the host cell genome, also referred to as "loop-in." In some implementations, one or more markers are then removed ("loop-out"). Liquid-based workflows that may be implemented in the context of Strain Build are described below with respect to FIGS. 2-14.

The cells confirmed to have been modified (by e.g. Next Generation or Sanger sequencing) may then be evaluated in an operation 105. For example, the modified strain can be evaluated based on the yield of a desired chemical or other relevant metric. Testing can involve evaluating the performance of one or more strains in microtiter plates and fermentation tanks, or in any other cell cultivation environment. Information from operation 105 may be used to generate new proposed genetic modifications to repeat the operations in the flowchart 100. In high throughput strain engineering, a process as represented by flowchart 100 may be performed hundreds or thousands of times, in parallel and/or sequentially. The liquid-based workflows described herein may provide significant time savings, on the order of days for each iteration of the process.

Although the liquid-based workflows are described below chiefly in the context of high throughput strain engineering, they may be used in any application in which selection, counter-selection, and/or isolation of clonally pure populations of cells is desired.

Liquid-Based Workflow for Strain Build

Implementations of the methods described herein relate to selection, counter-selection, and/or isolation of genetically edited micro-organisms. The edited micro-organisms may be produced after the transformation of extraneous DNA by any of a variety of techniques, including electroporation, conjugation, transfection, transduction, or any other kind of DNA transformation. The editing may be achieved by any method of DNA editing, including but not limited to single and double recombination, recombinase-assisted recombination, intron-assisted recombination and nuclease-assisted recombination. The liquid-based workflows described herein may be implemented in a variety of contexts in strain engineering.

Figure 2:
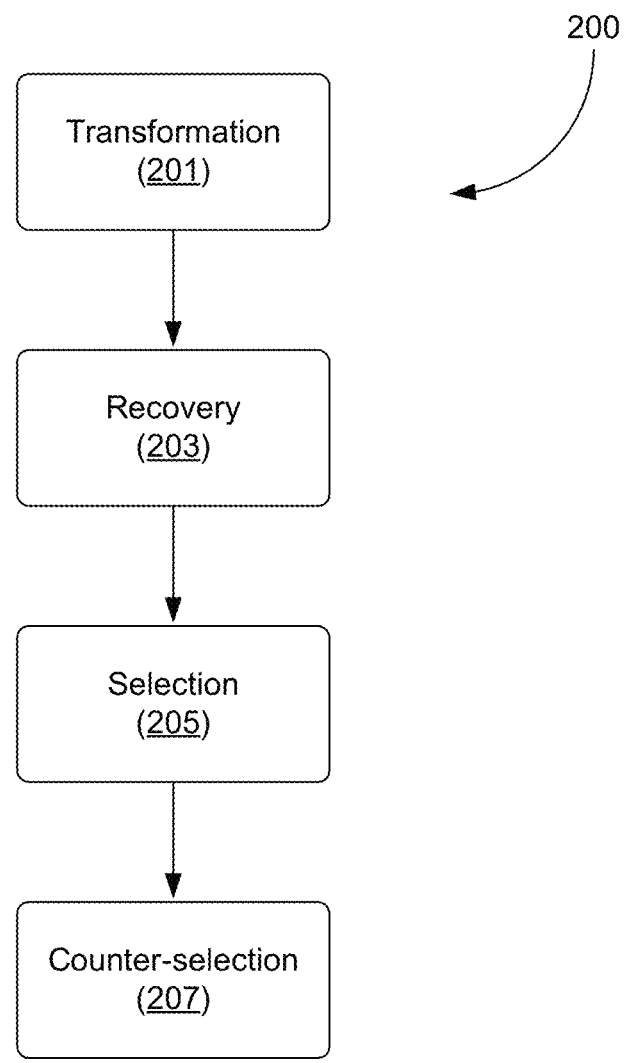
FIG. 2 is a flowchart depicting a high-level process for integrating a target DNA sequence into a host strain.

FIG. 2 is a flowchart depicting a high-level process for integrating a target DNA sequence into a host strain ("Strain Build"). It should be noted that the process depicted in FIG. 2 is an example of a method in which the liquid-based workflows described herein may be implemented. The flowchart represented by reference number 200 begins with an operation 201 in which an extraneous DNA sequence is transformed into the host strain. In some embodiments, transformation includes electroporation.

Operation 201 may produce a mixed population of cells, the mixed population including mutant cells that include the extraneous DNA sequence and non-mutant cells. The mutant cells may have a target DNA sequence as well as one or more markers integrated into their genomes. The target DNA sequence is flanked by regions of DNA homologous to the targeted region of the genome. These homologous regions facilitate genomic integration via DNA recombination, and, once integrated, form direct repeat regions designed for looping-out the vector backbone DNA in subsequent steps.

Figure 3:
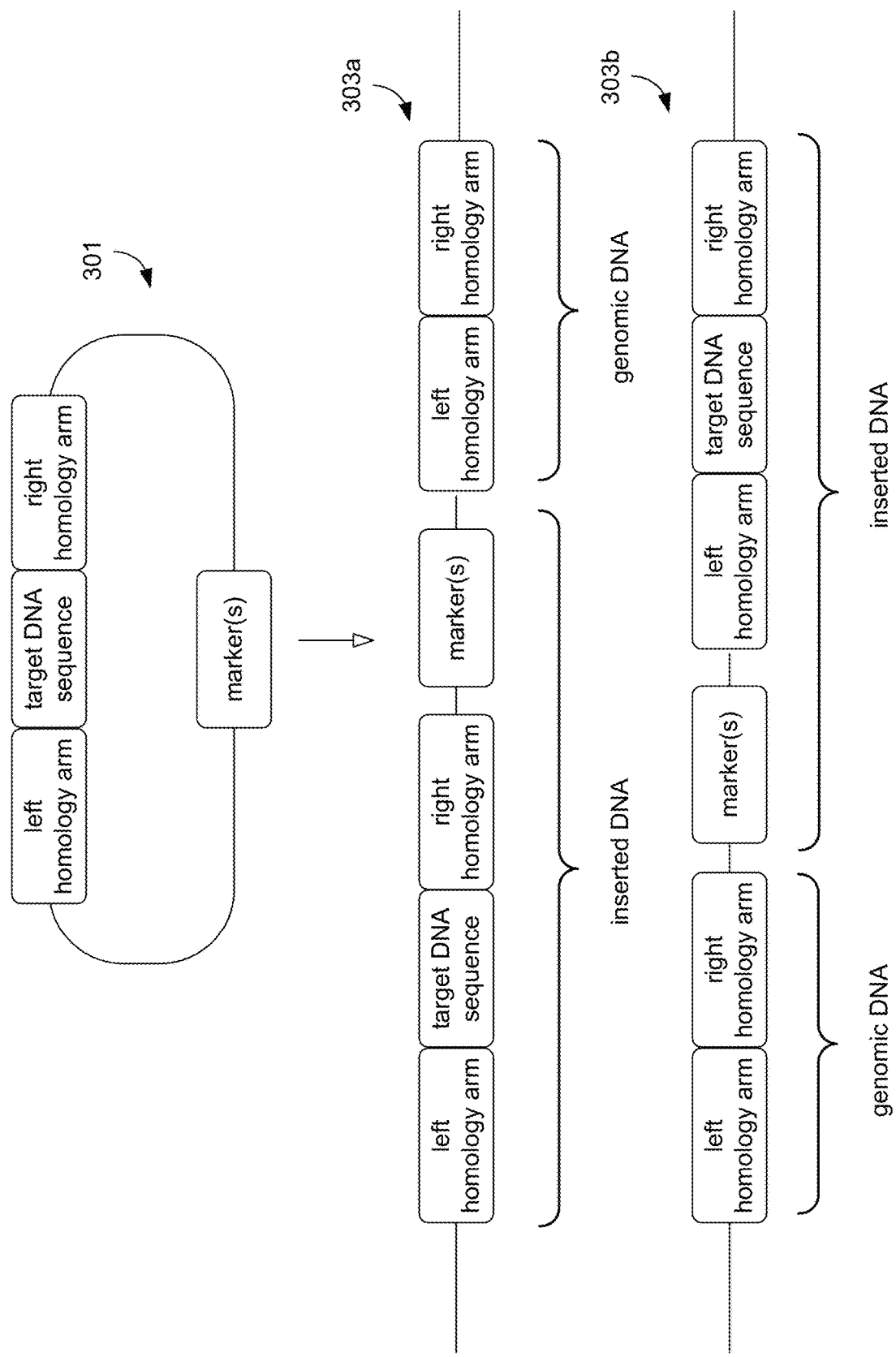
FIG. 3 is an illustration of example sequences of mutant cells produced by transformation of host cells with a plasmid in a strain build process.

FIG. 3 shows an example of sequences (303a and 303b) of mutant cells produced by transformation of host cells with a plasmid 301. The mutant cells include the target DNA sequence and one or more markers as indicated. It should be noted that the exogenous DNA may be integrated into the chromosome of the non-mutant cells on the left homology arm or the right homology arm of the genomic DNA, as shown, at 303a and 303b, respectively. The plasmid is a suicide (i.e., replication incompetent) plasmid such that non-integrated plasmids do not replicate in the host.

In some embodiments, the one or more markers include a selection marker, which codes for resistance to a selection agent. In one example, a mutant cell includes a selection marker that encodes resistance to kanamycin. Further examples of selection markers are provided below. In some embodiments, the one or more markers include a counter-selection marker, which codes for one or more peptides, proteins or small molecules, or is a DNA or RNA molecule, that leads to cell death in counter-selective conditions. In some examples, a mutant cell includes a counter-selection marker sacB, which codes for a protein (enzyme) that converts sucrose to levan. This leads to cell death in the presence of sucrose due to the toxicity of levan. Further examples of counter-selection markers are also provided below.

Returning to FIG. 2, the cells are allowed to recover (203) and then selection is performed to enrich the mutant cells relative to the non-mutant cells. (205). This operation may involve culturing the mixed population in the presence of a selection agent that causes cell death of the non-mutant cells. As described further below, selection is performed in liquid media and without generating clonal populations on a plate that contains a solid material and selection agent for cell growth.

Figure 4:
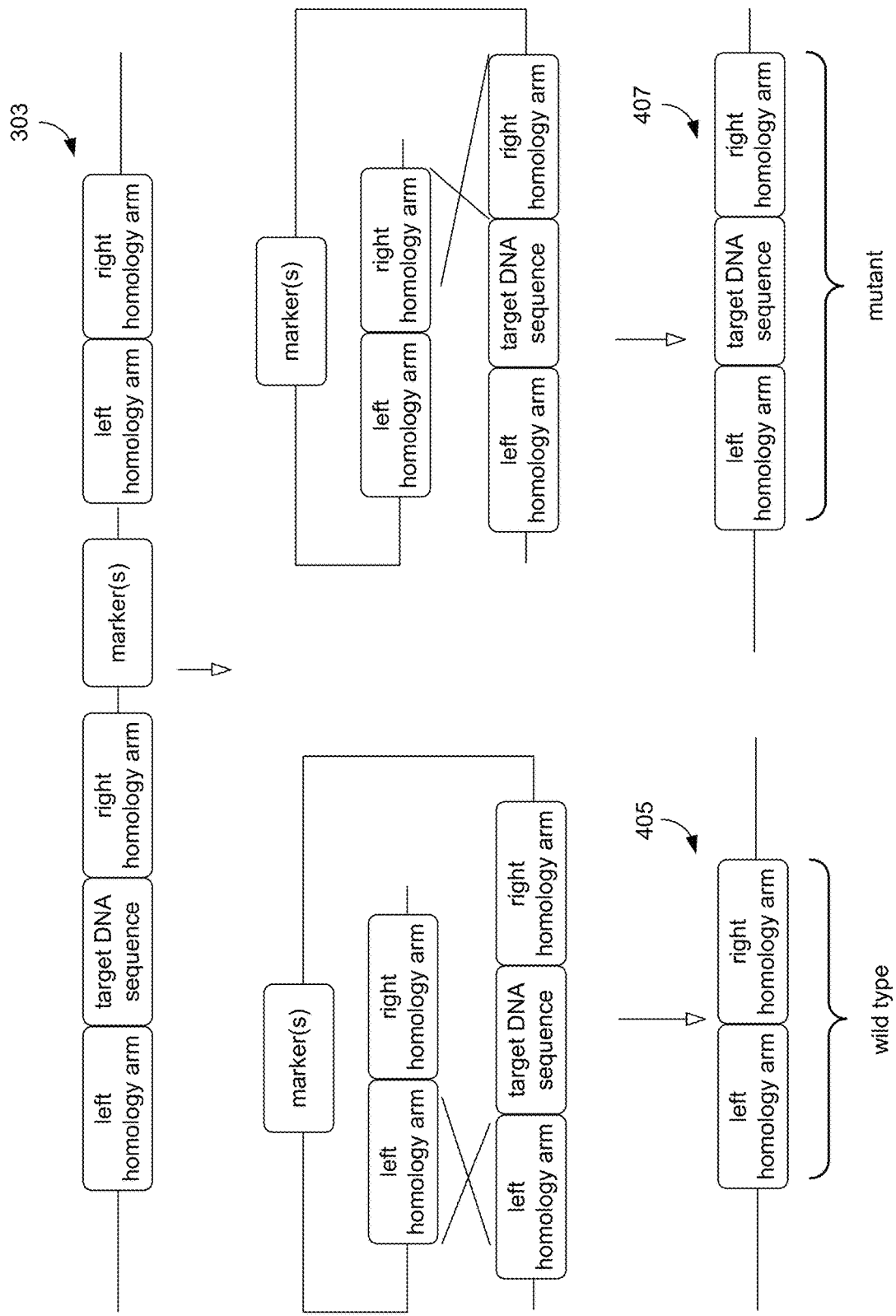
FIG. 4 is an illustration of an example of removing one or more markers from host cells in a strain build process.

Outgrowth under counter-selective conditions is then performed in an operation 207. In some embodiments, operation 207 includes removing one or more markers. For example, outgrowth in sucrose-containing media can enrich the liquid media for cells that do not include the sacB marker, after having lost it due to a recombination episode. FIG. 4 depicts an example of removing the one or more markers from host strains. Recombination of a mutant sequence 303 allows direct repeat regions of the inserted DNA and host genome to "loop-out" producing base strain cells (sequence 405) and mutant cells (sequence 407) without the markers. As described further below, in some embodiments, counter-selection is performed in liquid media and without generating clonal populations on a plate that contains a solid counter-selection agent.

Figure 5:
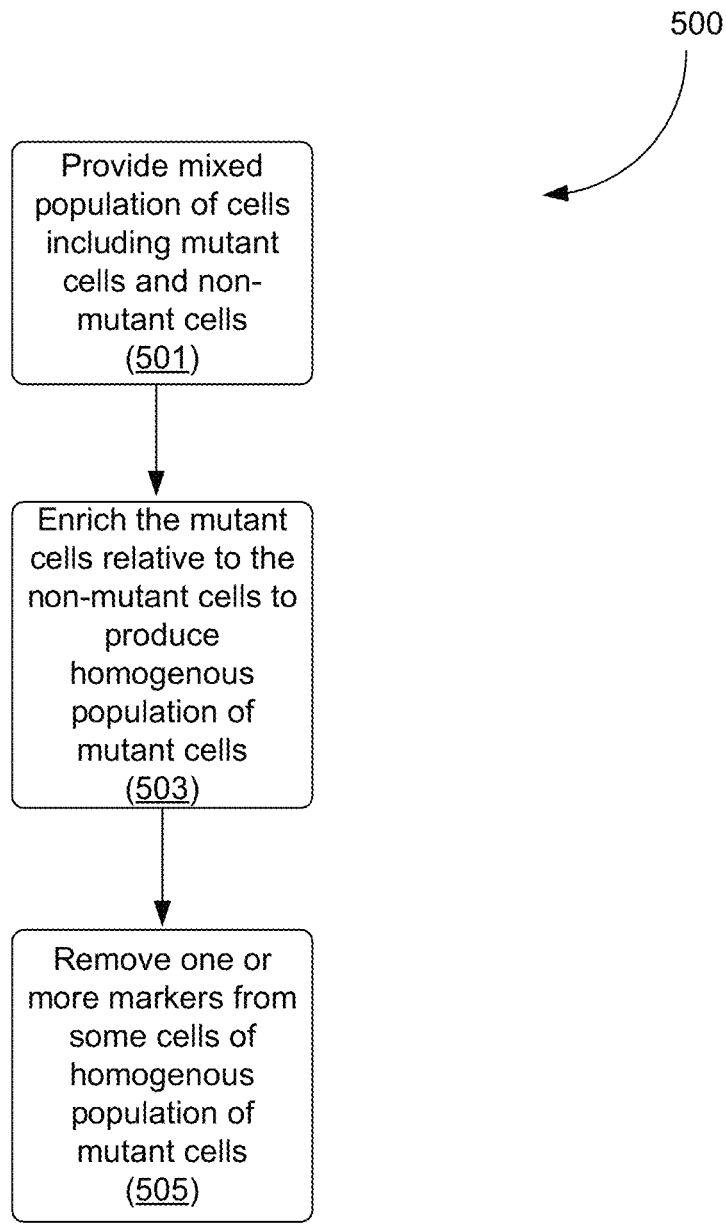
FIG. 5 is a flowchart depicting a liquid-based workflow for selection and counter-selection of cells.

FIG. 5 is a flowchart depicting a liquid-based workflow for selection and counter-selection of cells. The workflow depicted in FIG. 5 may be used to go from integration of the target DNA and markers into the genome ("loop-in") to removing the markers ("loop-out") and additional plasmid DNA sequences without generating colonies on a plate or requiring colony picking.

The flowchart represented by reference number 500 begins with an operation 501 in which a mixed population of cells including mutant cells and non-mutant cells is provided. The mixed population may be generated by any appropriate method of introducing extraneous DNA into cells. The mutant cells include a selection marker and a counter-selection marker, provided in the extraneous DNA. The mixed population of cells may be received from a high-throughput electroporation system in some embodiments. For example, it may be received from a high throughput electroporation system such as VWR® High-throughput Electroporation System, BTX™, Bio-Rad® Gene Pulser MXcell™ or other multi-well electroporation systems that can transform wells in 96-well, 384-well, or other multi-well plates.

The mutant cells are then enriched relative to the non-mutant cells to produce a homogenous population of mutant cells in an operation 503. Producing a homogenous population in liquid enables transitioning from loop-in to loop-out without plating on solid media, colony picking, or isolating the cells. Operation 503 includes selection in liquid media that includes a selection agent.

Selection in liquid media has challenges that are not present or are reduced with agar-based selection. In particular, there may be different types of "background" or non-mutant cells that can impair the selection process; these include types referred to as "spontaneous mutants," "persister cells," and "plasmid-based persister cells."

Spontaneous mutants are cells that spontaneously develop resistance to the selection agent but do not contain the extraneous DNA, despite surviving in the presence of the selective agent as if they did. Persister cells are cells that are alive but metabolically inactive and thus not affected by the selection agent.

Figure 7:
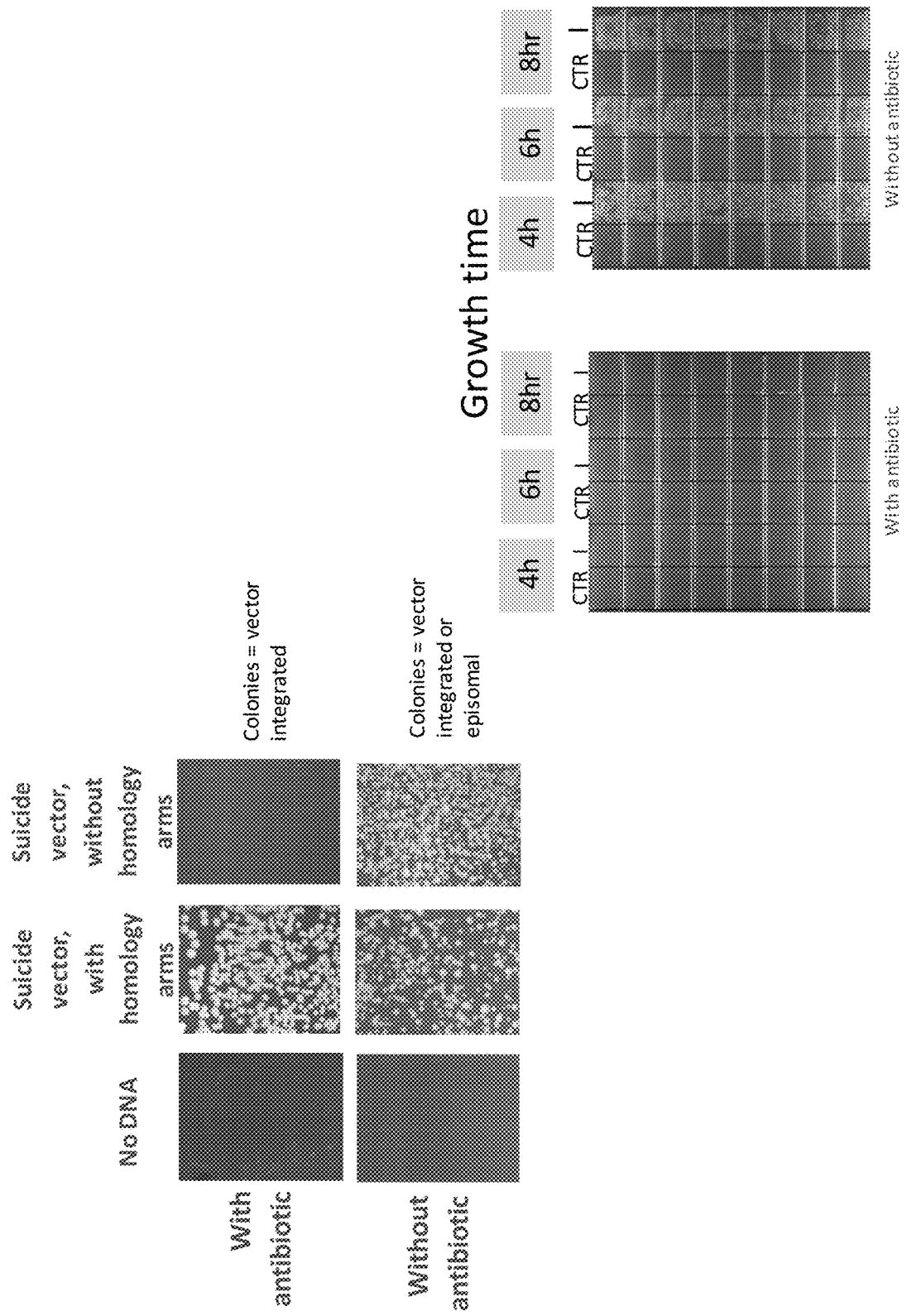
FIG. 7 shows images of plate-based selection of cells transformed with a suicide, non-replicative plasmid after recovery and its presence in liquid medium with selection agent.

Plasmid-based persister cells are cells that carry a non-integrated, non-replicative plasmid that includes the selection marker. The cells are resistant to the selection agent but cannot replicate the plasmid. FIG. 7 shows images of plate-based selection of cells transformed with a suicide plasmid after recovery in non-selective medium, followed by outgrowth in liquid medium containing a selection agent (kanamycin), for a given time period. In the presence of a selection agent in liquid, such as kanamycin, plasmid-based persister cells maintain the suicide plasmid in the episome, giving these cells resistance to said selection agent. The number of plasmid-based persister cells is constant throughout the time course experiment in FIG. 7 due to their incapacity to replicate the plasmid. As can be seen in the left image, no colony forming units (CFUs) are present when the liquid culture is plated on agar including Kan 50, this indicates that there are no loop-in cells on the plates. When the liquid culture is plated to agar without the selection agent, the plasmid-based persister cells can replicate, forming CFUs as can be seen in the right image. Plasmid-based persister cells are not observed on plate-based selection because they cannot form colonies so they will not be detected and collected, but their presence affects the liquid selection of the mutant cells because they will be present and obfuscate the true loop-outs once the initial selective agent is removed. In some embodiments, for example, where integration of a vector into the genome is unaided by enzymes, a post-transformation population may have hundreds as many plasmid-based persister cells as mutants having the desired genomic mutation or mutations. In some embodiments, removing or significantly reducing the plasmid-based persister cells during liquid selection is important. This is because if any plasmid-based persister cells remain once the selection agent is removed (e.g. upon transition to counter selective media), they can grow and dominate the population rendering extremely difficult the process of detecting true mutants.

Figure 6:
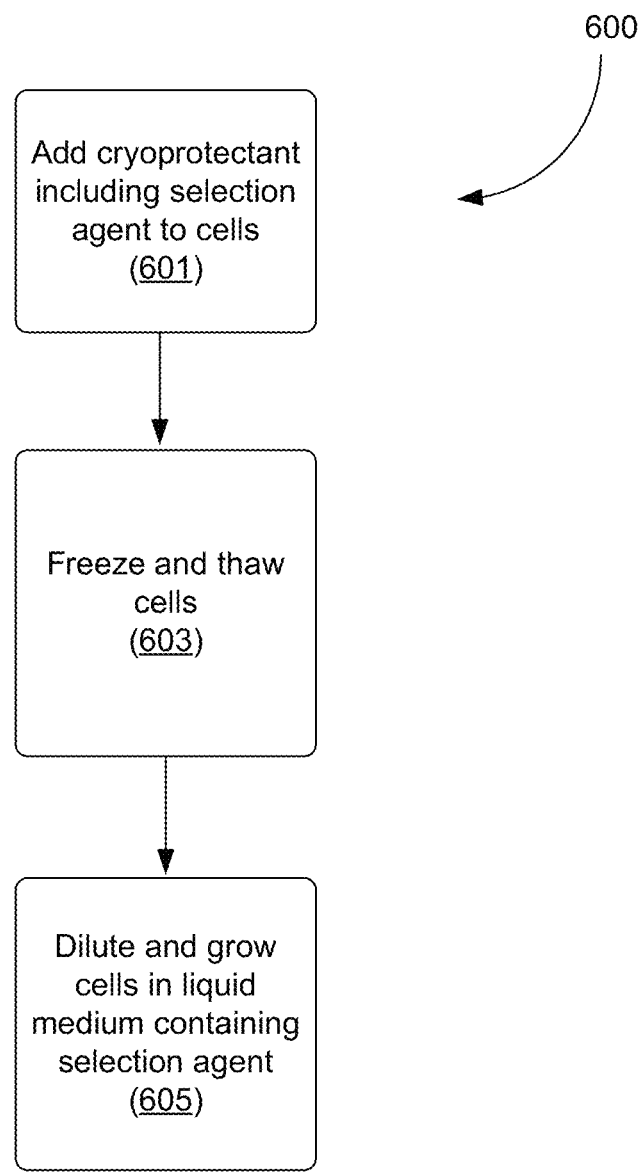
FIG. 6 is a flowchart depicting a liquid-based workflow for selection of mutant cells in liquid.

To remove the background cells during selection, one or more liquid-based processing operations may be employed. In some embodiments, freezing and thawing a liquid suspension of cells removes certain background cells. In some embodiments, dilution coupled with outgrowth in liquid removes, by dilution, certain background cells. FIG. 6 is a flowchart depicting a liquid-based workflow for selection of mutant cells in liquid. The workflow in FIG. 6 may be used to produce a homogenous population of mutant cells as shown in operation 503. The flowchart represented by reference number 600 begins with an operation 601 in which a cryoprotectant including a selection agent is added to a population of cells including mutant cells and non-mutant cells. The mixed population may include one or more background cell types including spontaneous mutants, persister cells, and plasmid-based persister cells. In an example, a suspension including the cells is added to a Brain Heart Infusion (BHI) or Super Optimal broth with Catabolite repression (SOC) medium containing e.g. 50 ug/mL of kanamycin and a cryoprotectant.

The cells are then frozen and subsequently thawed in an operation 603. This may be performed immediately after operation 601 and involves taking all or an aliquot of the suspension, to which a cryoprotectant was previously added or will be added immediately before, and freezing it. Example freezing conditions are −80° C. for 1 hour. The freezing is sufficient such that thawing the metabolically inactive cells transitions them to a metabolically active state in which they are susceptible to the selection agent. Freezing and thawing spontaneous mutant cells, and their subsequent re-exposure to the selective agents, results in a deadly stress that allows for their removal from the population. The remaining cells may then be grown in a liquid medium including the selection agent. The cells are then diluted and grown in a liquid medium containing the selection agent an operation 605. This results in a predominantly mutant population of cells, which keep doubling in the presence of the selection agent.

Figure 9:
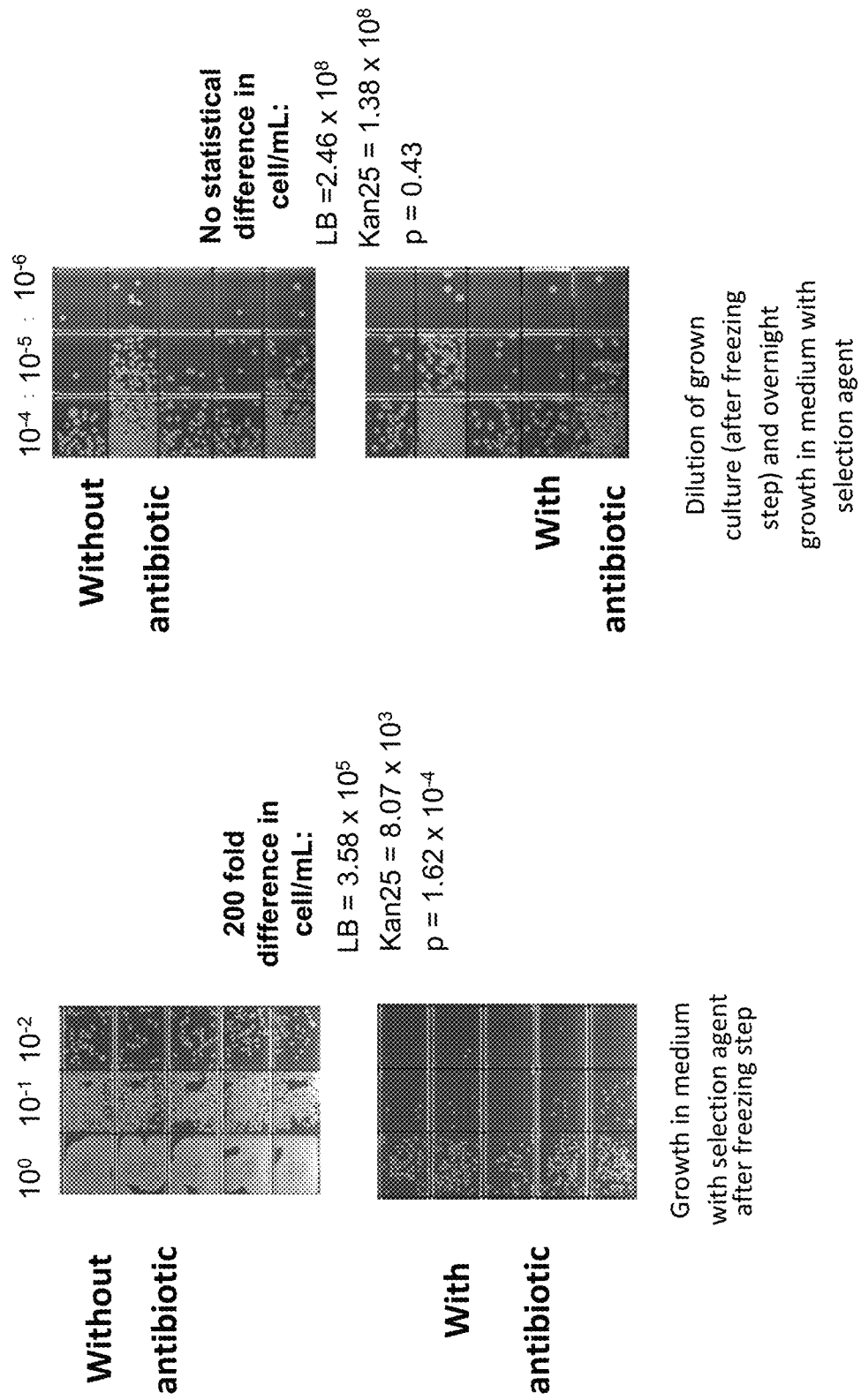
FIG. 9 shows the results of plate-based selection of mutants compared to non-selective growth after initial growth and selection steps, and after dilution and overnight growth in liquid with selection agent.

Plasmid-based persister cells can be removed by dilution coupled with growth of the suspension in a selective medium. FIG. 9 shows the total composition of the liquid population (LB) and its mutant fraction (LB Kan25) 8 DTs (doubling times) after the freeze/thaw step and after dilution and overnight growth in liquid. Additionally, FIG. 9 shows the results of plate-based selection in addition to the liquid-based selection of mutants (lower left image) compared to a partial liquid selection (upper left image). There is a 200-fold difference in cell/mL without the selection agent, which represents the difference in plasmid-based persister cells to loop-in cells. After dilution, and overnight growth of the suspension, there is no statistical difference between growth on selective media (lower right image) and growth on non-selective media (upper right image). This indicates that all of the plasmid-based persister cells (and other non-loop-in cells) have been eliminated or reduced to insignificant numbers, and the large majority, if not all, of the population is composed of mutant cells.

Figure 8:
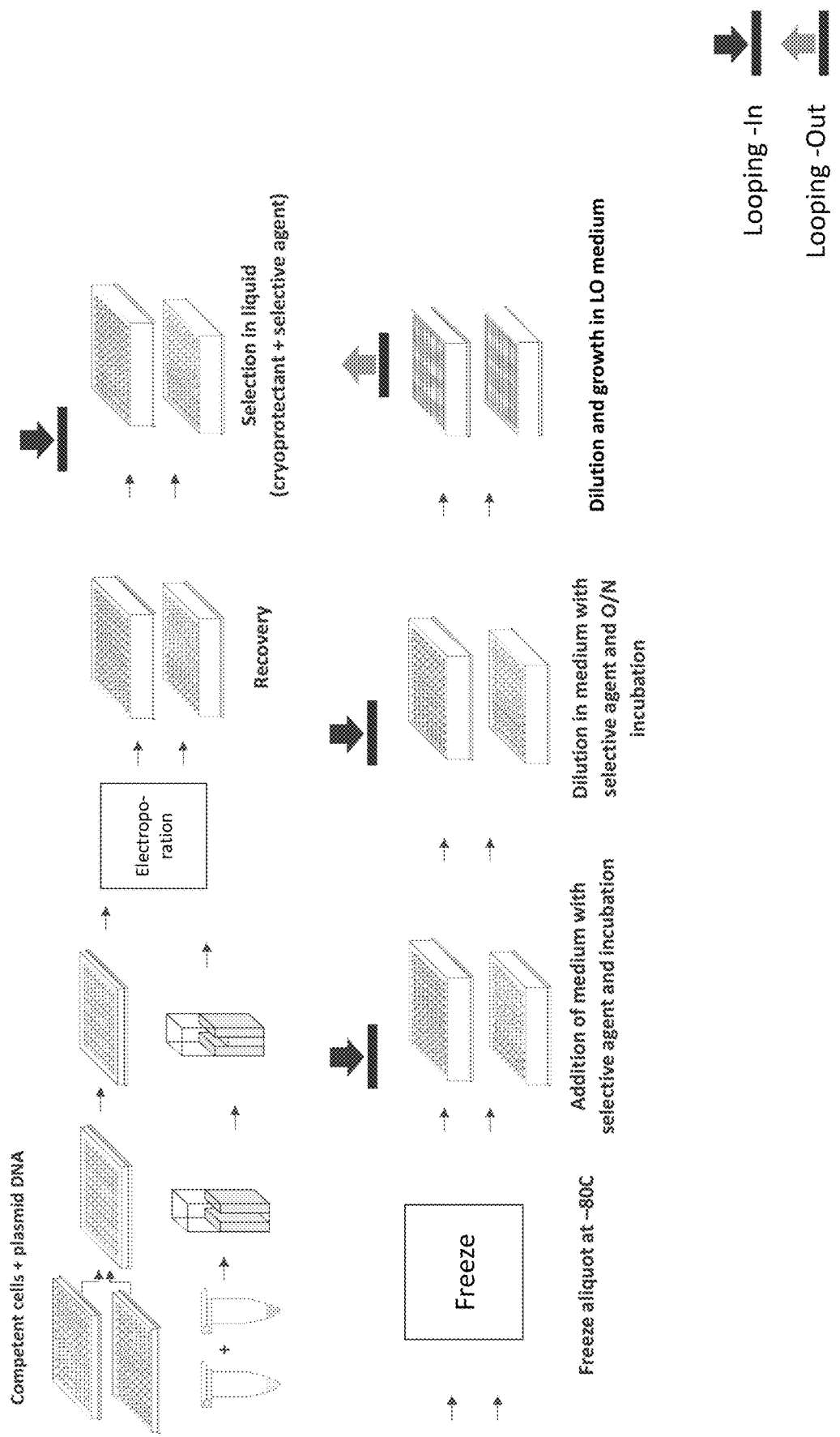
FIG. 8 shows an example of a liquid-based workflow according to the method depicted in FIG. 6.

FIG. 8 shows an example of a liquid-based workflow according to the method depicted in FIG. 6. As indicated in FIG. 8, the production of a homogenous population of mutant cells that include target DNA incorporated into their genomes may be obtained in a 24 hour period for E. coli. Cells are mixed with DNA to be inserted, then electroporated to introduce the DNA into the cells. The post-transformation cells are recovered in SOC liquid media. Immediately after recovery, a Kan50 selection agent in glycerol (cryoprotectant) is added. An aliquot of the cells is frozen at −80 C for 2 DTs. This is followed by a first dilution (1:3) in SOC containing Kan50 for 8 DTs and a second dilution (1:100) in LB containing Kan50 with overnight growth. The cells are then ready for loop-out. Colony PCR of cells after performing a liquid-based workflow as shown in FIG. 8 showed that the overnight (O/N) loop-in liquid population is all loop-in cells, with no or insignificant numbers of background and base strain cells.

To perform an effective selection for a given system, the liquid-based workflow in FIG. 6 may be used, with the parameters of recovery time, liquid medium, antibiotic (or other selection agent) concentration, incubation time, dilution factor, and selection time tuned as appropriate. Example recovery times of less than 1 DT to more than 10 DTs may be used. The medium may be defined (e.g., Minimal medium #63) or complex (e.g., Lysogeny Broth). In some embodiments, a first dilution (e.g., 1:4 or 1:8) is followed by a second dilution (e.g., 1:50 or 1:100).

Figure 10:
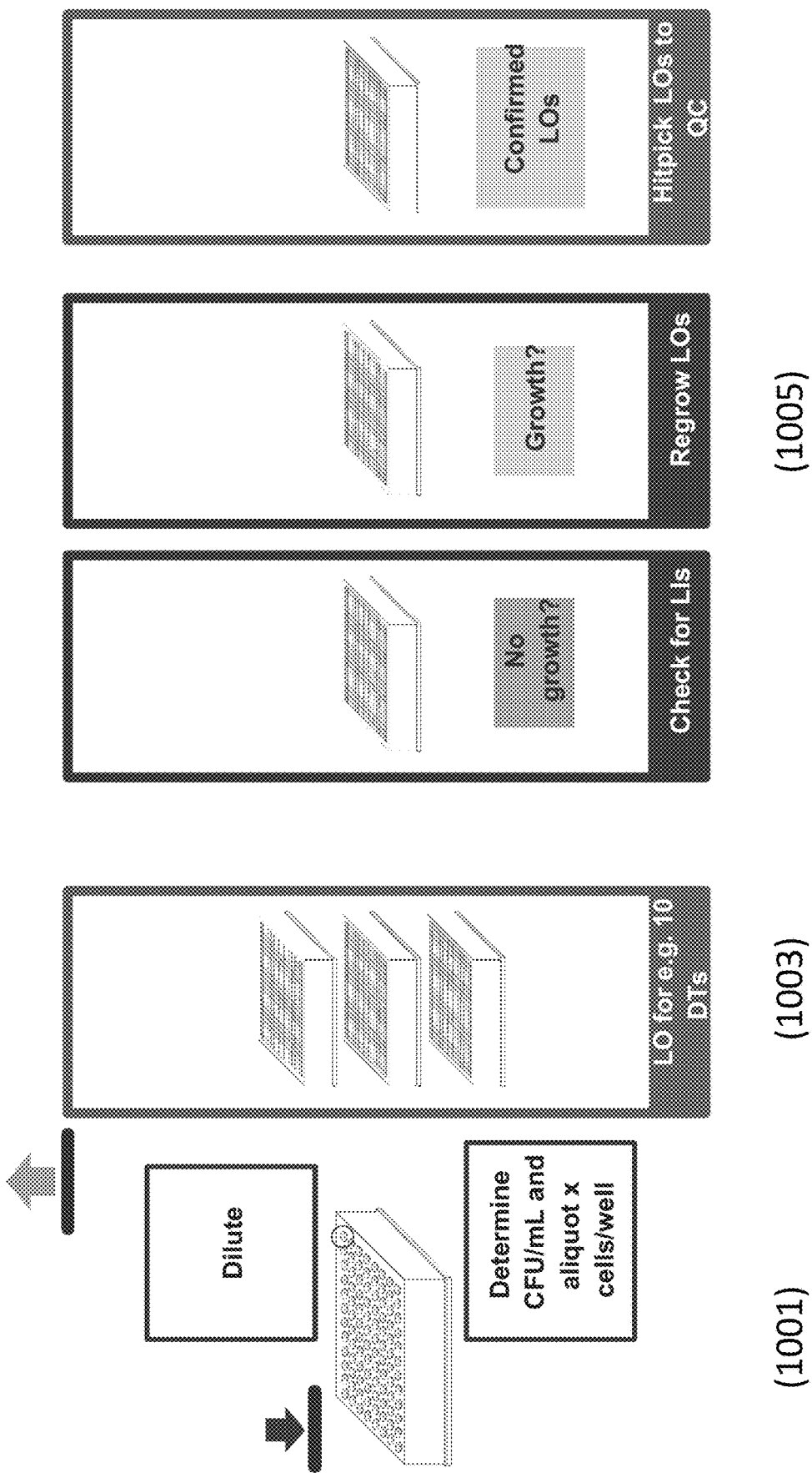
FIG. 10 is an example of a liquid-based workflow for removal of counter-selective markers in liquid.

Returning to FIG. 5, after the homogenous population of mutant cells is produced, the one or more markers are removed from some cells of the homogenous population (505). As indicated above, this is referred to as "loop-out". FIG. 10 is an example of a liquid-based workflow for removal of markers in liquid. The workflow begins with an operation 1001 in which a suspension of homogenous population of mutant cells that include a counter-selection marker is received. The homogenous population may be produced by outgrowth in a liquid medium including a selection agent. In some embodiments, the homogenous population can be produced by a method including one or both of freezing and thawing cells and dilution and outgrowth in the presence of a selection agent to remove non-mutant cells as described above with reference to FIGS. 6-8. Also, in some embodiments, the mutant cells have a selection marker and a counter-selection marker integrated into their genomes, as described above. The one or more markers may be integrated on a left or right homology arm as described above with respect to FIG. 3.

The substantially homogenous population of mutant cells is cultured in liquid under counter-selective conditions to produce second mutant cells (1003). The second mutant cells (also referred to as loop-out cells) may include a target DNA sequence but no markers. An example is shown in FIG. 4 at 407.

Operation 1003 may be performed for a time long enough for the loop-out process to occur, but without allowing so much time that growth rate differences (e.g. between the base strain and the mutant loop-out cells) allow the base strain to take over the population. For example, allowing cells to grow overnight in liquid media may lead to mostly base strain cells. In some implementations, operation 1003 may be performed for as few as 2 DTs and as many as 100 DTs, for example. Operation 1003 can be skipped if one is employing a limiting dilution process for obtaining clonally isolated populations of the second mutant cells. Nonetheless, outgrowth of looped-out (second mutant) cells would still be performed, even if for only a low number of DTs.

Clonally isolated populations of the second mutant cells are produced in liquid in an operation 1005. In some embodiments, producing a clonally isolated population of the mutants involves a limiting dilution process in which the number of cells in the diluted sample (e.g., a well in a multi-well plate) is no more than a threshold number (e.g., 1, 2, etc.) due to the statistical distribution of the cells in the dilution.

Figure 11:
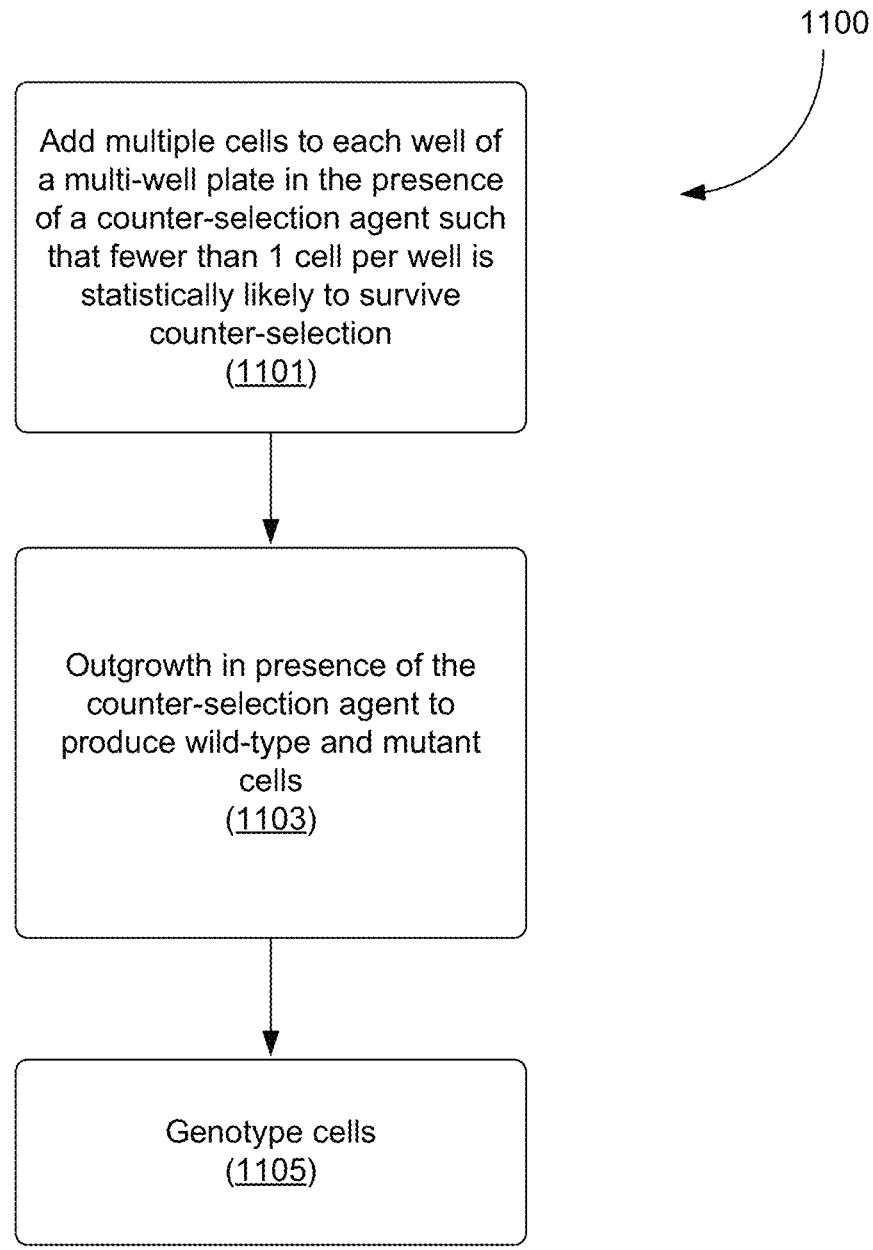
FIG. 11 is a flowchart depicting a method for isolating clonally pure populations of cells in liquid using limiting dilution.
Figure 12:
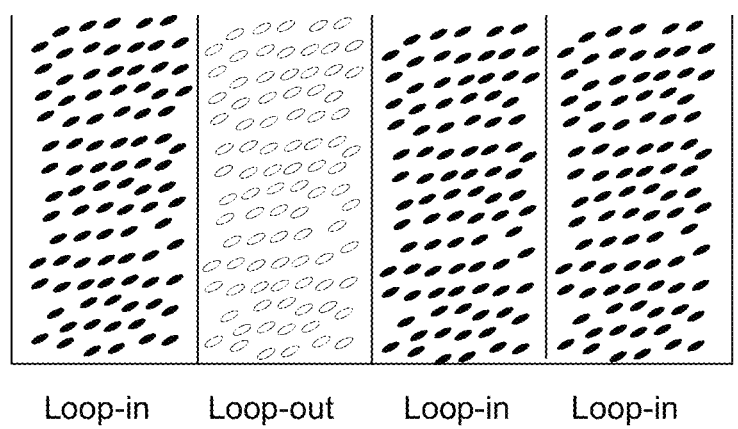
FIG. 12 illustrates a schematic example of isolation of a clonally pure population of loop-out mutant cells by a limiting dilution method.

As illustrated in FIG. 4, from a loop-in cell, counter-selection can produce base strain cells or loop-out (mutant cells). Thus, the population of cells in counter-selection media will have mutant cells including a counter-selection marker (loop-in cells) that will die, mutant cells without the counter-selection marker (loop-out cells), and cells that revert to the base strain (looped-out in the same homology arm as they looped-in). In some embodiments, most of the population will be loop-in cells. FIG. 11 is a flowchart depicting a method for isolating clonally pure populations of cells in liquid using limiting dilution. The flowchart represented by reference number 1100 begins with an operation 1101 in which multiple cells are put in each well in the presence of a counter-selection agent such that no more than one cell per well is statistically likely to survive counter-selection. For example, the limiting dilution may be performed such that one of every four wells or one of every ten wells has a cell that survives counter-selection. Outgrowth in the presence of the counter-selection occurs in an operation 1103. This leads to the death of loop-in cells. In wells that have a cell that survives counter-selection, that cell will take over the population. This is illustrated schematically in FIG. 12, which shows a schematic example of four wells, with one having a clonally pure population of loop-out cells. It should be noted that in the unlikely event both a mutant cell and base strain cell survive counter-selection, the base strain cell may take over the population. In some embodiments, the cells may then be genotyped in an operation 1105. In this example, operation 1105 may be used to determine if the cells in each well (i.e., each isogenic population) are base strain or mutants.

Figure 13:
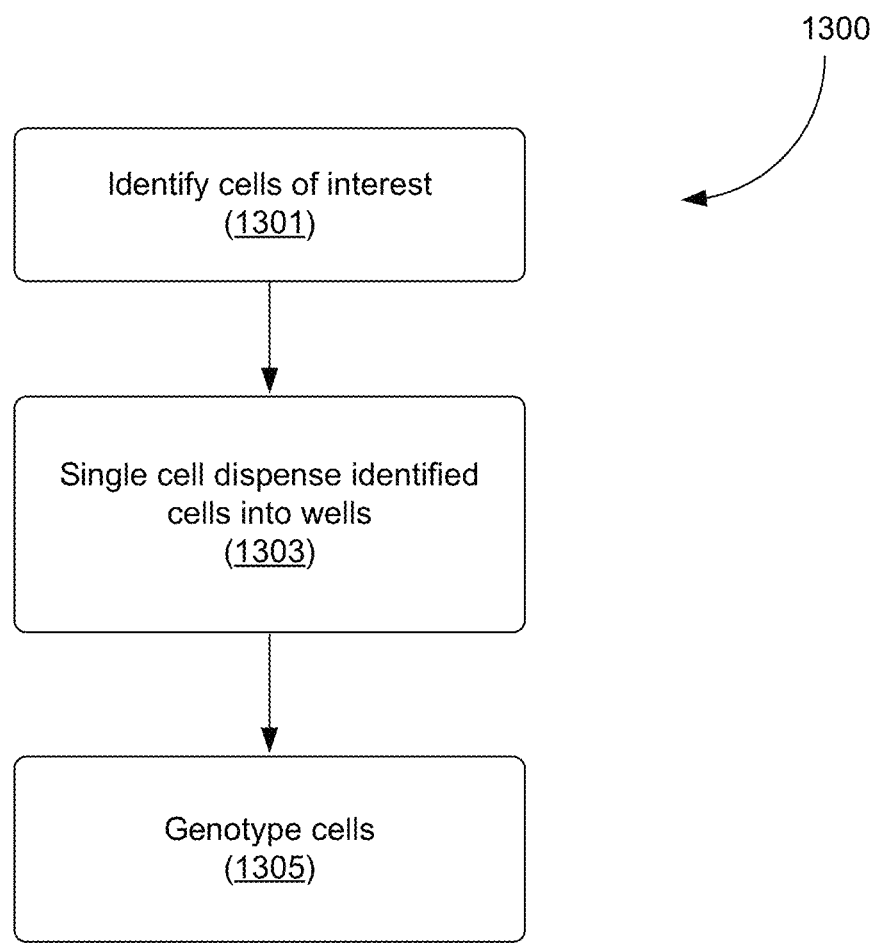
FIG. 13 is a flowchart depicting a method for isolating clonally pure populations of cells in liquid using cell sorting.

In some embodiments, producing a clonally isolated population of the mutants involves sorting the cells. FIG. 13 is a flowchart depicting a method for isolating clonally pure populations of cells in liquid using sorting. The flowchart represented by reference number 1300 begins with an operation 1301 in which cells of interest are identified. In the example of loop-outs, the cells of interest are those without the markers or plasmid backbone. In some embodiments, operation 1301 involves optical identification. For example, the plasmid may include a fluorescent marker such as green fluorescent protein (GFP). Cells that do not include the GFP are identified as not having a marker or plasmid backbone (and thus these cells are either mutant or base-strain revertant looped-out cells) and sorted using fluorescent activated cell sorting (FACS). In some embodiments, operation 1301 involves a viability stain, with the cells first sufficiently exposed to counter-selection agent to kill loop-in cells. The plasmid may include a fluorescent reactive dye or other marker. Cells that are alive may then be sorted using a LIVE/DEAD fixable viability stain from ThermoFisher or other appropriate viability stain or dye.

Figure 14:
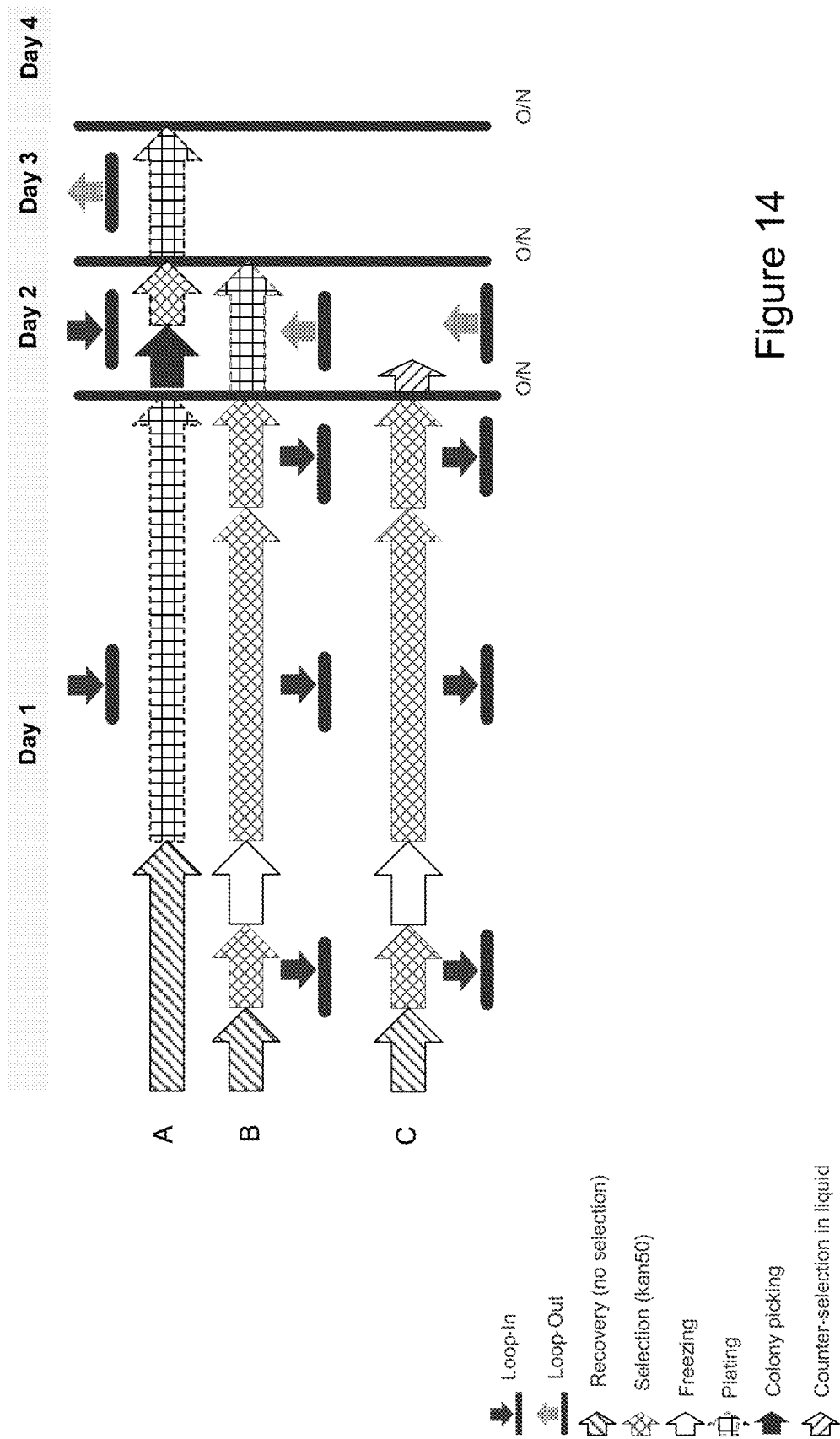
FIG. 14 provides a schematic illustration of example time frames for three processes: A) loop-in and loop-out using plating on solid media; B) liquid-based loop-in and loop-out using plating on solid media, and C) liquid-based loop-in and loop-out.

Once the cells of interest are identified, the method may proceed with single cell dispensing into a well in an operation 1303. A single cell dispenser such as Cellen.ONE or FACS may be used to put a single cell into each well. As noted above, loop-ins may dominate the mixed population; it is not practical to dispense each cell into a well for genotyping. However, by sorting the cells before single cell dispensing, only cells of interest will occupy a well. In some embodiments, the cells may then be genotyped in an operation 1305 to determine if the cells in each well (isogenic population) are base strain or mutants FIG. 14 provides a schematic illustration of example time frames for three processes with an organism like *E. coli*: A) loop-in and loop-out using plating on solid media; B) liquid-based loop-in and loop-out using plating on solid media, and C) liquid-based loop-in and loop-out. As can be seen by comparing process (A) to process (B), 24 hours may be saved by doing liquid-based loop-in, even in implementations in which loop-out is performed using counter-selection on a solid medium. In the morning of Day 2, the loop-in selection process is complete and the cells are ready to proceed to loop-out. Comparison of process (B) to process (C) shows significant additional time savings (e.g., 24 hours vs 4 hours) by using liquid-based loop-out. For organisms that grow slower than *E. coli*, additional time savings would be realized.

Liquid-Based Workflow for DNA Build

Figure 15:
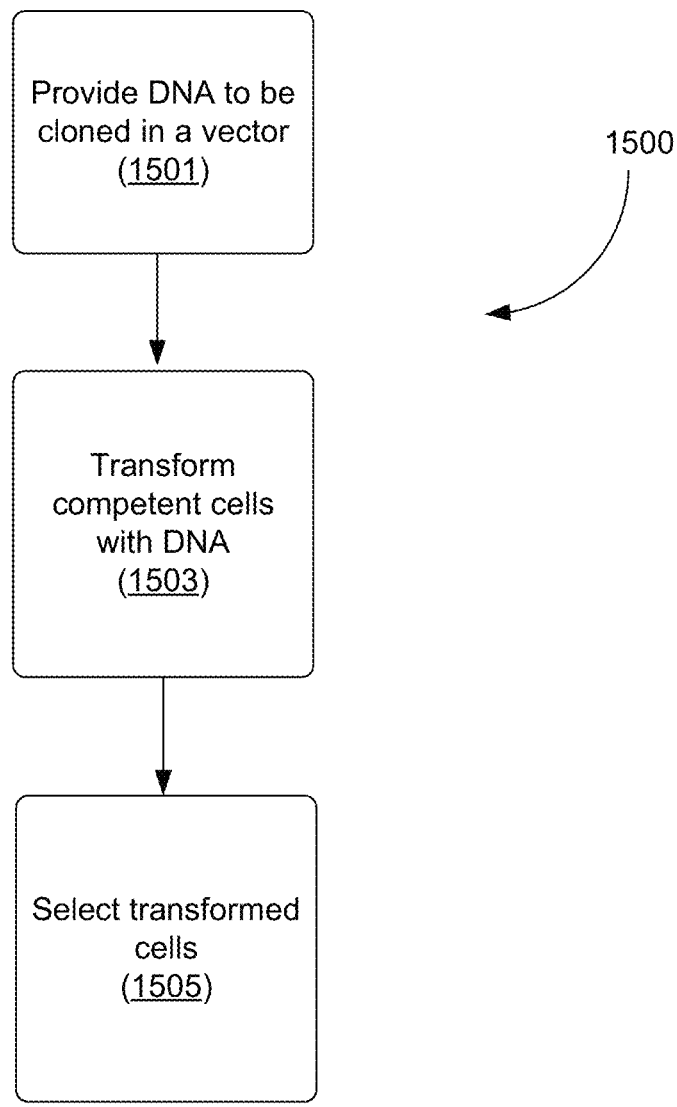
FIG. 15 is a flowchart depicting a high-level process for cloning a DNA sequence of interest.

FIG. 15 is a flowchart depicting a high-level process for cloning DNA ("DNA Build"). The process depicted in FIG. 15 is an example of a method in which the liquid-based workflows described herein may be implemented. The flowchart represented by reference number 1500 begins with an operation 1501 in which the DNA to be cloned is provided in a vector. In some embodiments, the vector is a plasmid assembled by and isolated from yeast. It is transformed into competent host cells, where it remains in the episome in an operation 1503. The transformed cells are then selected in an operation 1505. The cells grow in the presence of a selection agent, with the cells that do not include the vector dying. The transformed cells multiply, creating copies of the plasmid. In some embodiments, after further processing, the plasmids may be used for strain build as described above.

Figure 16:
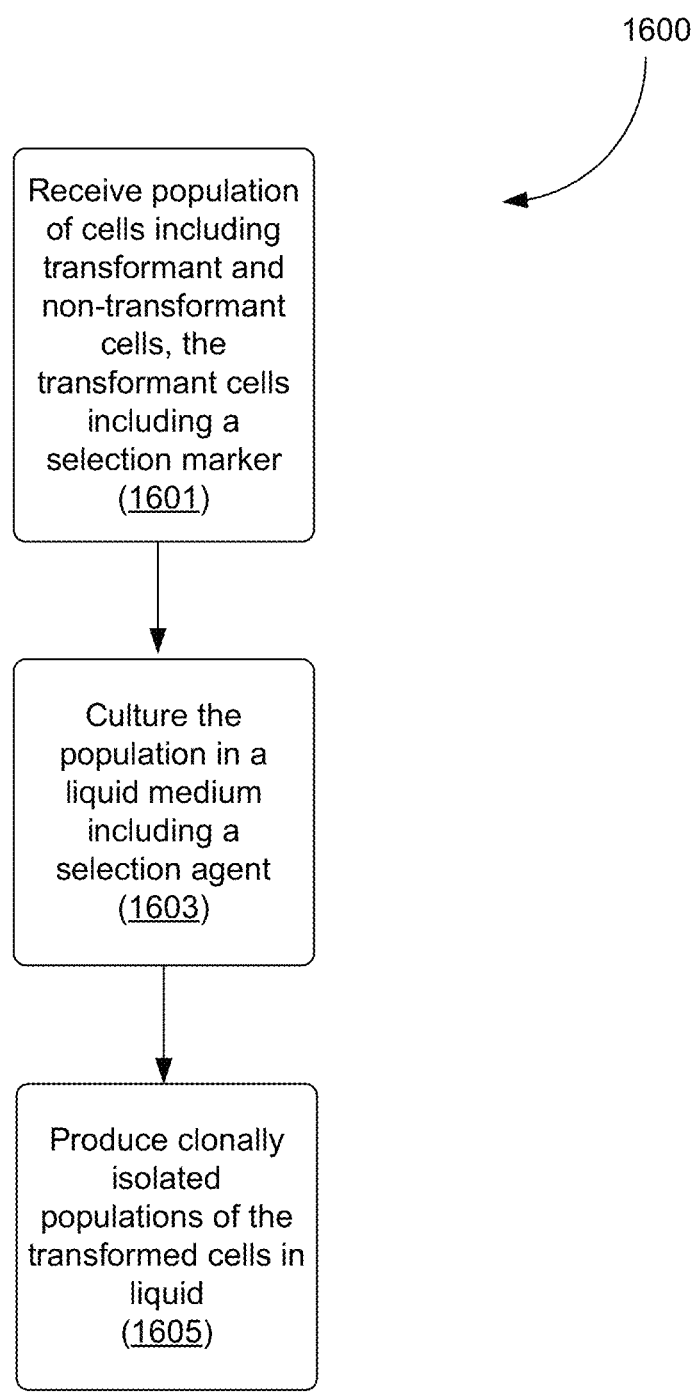
FIG. 16 is a flowchart depicting a liquid-based workflow for selection and isolation of clonally pure populations of cells.

FIG. 16 is a flowchart depicting a liquid-based workflow for selection and isolation of clonally pure populations of cells. The workflow depicted in FIG. 16 may be implemented as part of a DNA Build process as shown in FIG. 15 and be performed without plating cells suspension onto a solid selective medium to generate colonies that subsequently require picking. The flowchart represented by reference number 1600 begins with an operation 1601 in which a population of cells that include transformant cells and non-transformant cells is received. These cells allow for the replication of the vector transformed. The transformant cells include a vector having a selection marker. The population of cells is cultured in a liquid medium that includes a selection agent to select the transformant cells in an operation 1603. The surviving cells include the replicative plasmid, which is shared with daughter cells. Immediately after transformation, the number of transformant cells is far less than the non-transformants. Liquid selection may be performed for a time sufficient (e.g., 40 DTs) such that the fraction of transformant cells is high enough that sorting or performing a limiting dilution is not impractical. For example, liquid selection may be performed for a time such that the number of transformant cells is roughly equivalent to the non-transformant cells.

Then, clonally isolated populations of the transformant cells are produced in liquid in an operation 1605. In some embodiments, producing a clonally isolated population of the mutants involves a limiting dilution process in which the number of cells in the diluted sample is no more than a threshold number due to the statistical distribution of the cells in the dilution.

In some embodiments, producing a clonally isolated population of the transformant cells involves sorting the cells. A method as described with reference to FIG. 13 may be employed with a marker or other reporter incorporated into the vector in the transformant cells. For example, the plasmid or other vector may include GFP or other fluorescent marker. Cells that include the GFP are identified as including the vector and sorted using FACS. Also as described above with reference to the FIG. 13, in some embodiments, a viability stain or dye may be used with the cells first sufficiently exposed to the selection agent to the non-transformant marker. The cells that are alive may then be sorted using an appropriate viability stain or dye. Once the cells that include the vector are identified, the method may proceed with single cell dispensing into a well. In some embodiments, the cells may then be genotyped as part of a quality control process, for example.

Microbial Host Cells

The methods described herein are host-independent with any microbe that can be used to express introduced genes used. In some embodiments, the microbe is one that is readily cultured, such as, for example, a microbe known to be useful as a host cell in fermentative production of compounds of interest. In some embodiments, the cells are bacteria cells, and including gram positive or gram negative bacteria. Examples include *E. coli, C. glutamicum cells, Bacillus subtilus, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., *P. alcaligenes, P. citrea, Lactobacilis* spp. (such as *L. lactis, L. plantarum*), *L. grayi, E. faecium, E. gallinarum, E. casseliflavus*, and/or *E. faecalis* cells.

In some embodiments, the microbial host cells used in the methods described herein are filamentous fungal cells. (See, e.g., Berka & Barnett, Biotechnology Advances, (1989), 7 (2):127-154). Examples include *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp. (such as *A. oryzae, A. niger, A. sojae, A. japonicus, A. nidulans*, or *A. awamori*), *Fusarium* sp. (such as *F. roseum, F. graminum F. cerealis, F. oxysporuim*, or *F. venenatum*), *Neurospora* sp. (such as *N. crassa* or *Hypocrea* sp.), *Mucor* sp. (such as *M. miehei*), *Rhizopus* sp., and *Emericella* sp. cells. In particular embodiments, the fungal cell engineered as described above is *A. nidulans, A. awamori, A. oryzae, A. aculeatus, A. niger, A. japonicus, T. reesei, T. viride, F. oxysporum*, or *F. solani*. Illustrative plasmids or plasmid components for use with such hosts include those described in U.S. Patent Pub. No. 2011/0045563.

Yeasts can also be used as the microbial host cell in the methods described herein. Examples include: *Saccharomyces* sp., *Schizosaccharomyces* sp., *Pichia* sp., *Hansenula polymorpha, Pichia stipites, Kluyveromyces marxianus, Kluyveromyces* spp., *Yarrowia lipolytica* and *Candida* sp. In some embodiments, the *Saccharomyces* sp. is *S. cerevisiae* (See, e.g., Romanos et al., Yeast, (1992), 8 (6):423-488). Illustrative plasmids or plasmid components for use with such hosts include those described in U.S. Pat. No. 7,659,097 and U.S. Patent Pub. No. 2011/0045563.

In some embodiments, the host cell can be an algal cell derived, e.g., from a green algae, red algae, a glaucophyte, a chlorarachniophyte, a euglenid, a chromista, or a dinoflagellate. (See, e.g., Saunders & Warmbrodt, "Gene Expression in Algae and Fungi, Including Yeast," (1993), National Agricultural Library, Beltsville, Md.). Illustrative plasmids or plasmid components for use in algal cells include those described in U.S. Patent Pub. No. 2011/0045563.

In other embodiments, the host cell is a cyanobacterium, such as cyanobacterium classified into any of the following groups based on morphology: *Chlorococcales, Pleurocapsales, Oscillatoriales, Nostocales, Synechosystic* or *Stigonematales* (See, e.g., Lindberg et al., Metab. Eng., (2010) 12 (1):70-79). Illustrative plasmids or plasmid components for use in cyanobacterial cells include those described in U.S. Patent Pub. Nos. 2010/0297749 and 2009/0282545 and in Intl. Pat. Pub. No. WO 2011/034863.

Markers

Various selection marker genes are known in the art often encoding antibiotic resistance function for selection in prokaryotic (e.g., against ampicillin, kanamycin, tetracycline, chloramphenicol, zeocin, spectinomycin/streptomycin) or eukaryotic cells (e.g., geneticin, neomycin, hygromycin, puromycin, blasticidin, zeocin) under selective pressure.

Another class of selection markers relates to counter-selection marker genes that express toxic gene products that kill producer cells. These are generally referred to as counter-selection markers in the description herein. Examples of such genes include sacB, rpsL(strA), tetAR, pheS, thyA, lacY, gata-1, or ccdB. These and the corresponding counter-selection additives are described further in (Reyrat et al. 1998 "Counterselectable Markers: Untapped Tools for Bacterial Genetics and Pathogenesis." Infect Immun. 66 (9): 4011-4017).

Other marker systems allow for screening and identification of wanted or unwanted cells such as the blue/white screening system used in bacteria to select positive clones in the presence of X-gal or fluorescent reporters such as green or red fluorescent proteins expressed in successfully transformed host cells.

Transformation of Host Cells

In some embodiments, the vectors may be introduced into the host cells using any of a variety of techniques, including transformation, transfection, transduction, viral infection, gene guns, or Ti-mediated gene transfer (see Christie, P. J., and Gordon, J. E., 2014 "The Agrobacterium Ti Plasmids" Microbiol SPectr. 2014; 2 (6); 10.1128). Particular methods include calcium phosphate transfection, DEAE-Dextran mediated transfection, lipofection, conjugation or electroporation (Davis, L., Dibner, M., Battey, I., 1986 "Basic Methods in Molecular Biology"). Other methods of transformation include for example, lithium acetate transformation and electroporation See, e.g., Gietz et al., Nucleic Acids Res. 27:69-74 (1992); Ito et al., J. Bacterol. 153:163-168 (1983); and Becker and Guarente, Methods in Enzymology 194: 182-187 (1991).

High Throughput Liquid Handling

The methods and workflows described above may use apparatuses for high throughput liquid handling. The workflows described herein are generally directed to the use of 96- or 384-well microtiter plates, but as will be appreciated by those in the art, any number of different plates or configurations may be used. In addition, any or all of the operations described herein may be automated; thus, the methods may be completely or partially automated.

Liquid handling dispensers that may be employed include acoustic liquid handlers such as Labcyte Echo acoustic liquid handlers and BioSero Gen 5 ATS liquid handlers, Tekmatic BioSpot Nanoliter liquid handlers, and BioNex NanoDrop liquid handlers. Single cell dispensing systems such as Cellion's Cellen.ONE systems may be used for single cell dispensing. FACS systems may be used for sorting as described above.

Conclusion

None of the claims herein includes limitations presented in "means plus function" or "step plus function" form. (See, 35 USC § 112(f)). It is Applicant's intent that none of the claim limitations be interpreted under or in accordance with 35 U.S.C. § 112(f).

While the present invention has been particularly described with respect to the illustrated embodiments, it will be appreciated that various alterations, modifications and adaptations may be made based on the present disclosure, and are intended to be within the scope of the present invention. While the invention has been described in connection with the disclosed embodiments, it is to be understood that the present invention is not limited to the disclosed embodiments but, on the contrary, is intended to cover various modifications and equivalent arrangements included within the scope of the claims.

What is claimed is:

1. A method comprising:
providing a mixed population of cells, the mixed population comprising first mutant cells and non-mutant cells, the first mutant cells having a target DNA sequence integrated on a left or right homology arm, a selection marker, and a counter-selection marker integrated into their genomes, the selection marker coding for resistance to a selection agent and the counter-selection marker coding for one or more proteins that lead to cell death in counter-selective conditions and the non-mutant cells comprising one or more of: (a) metabolically inactive cells, (b) cells that spontaneously develop resistance to the selection agent but do not have the target DNA sequence, and (c) cells that carry a non-integrated plasmid comprising the selection marker and are resistant to the selection agent but that cannot increase in number;
in liquid, enriching the first mutant cells relative to the non-mutant cells in the mixed population to produce a homogenous population of first mutant cells; and
in liquid, removing the selection marker and the counter-selection marker from some cells of the population enriched for the first mutant cells.

2. The method of claim 1, wherein the method is performed without generating clonal populations on a plate containing solid growth medium and selection or counter-selection additives.

3. The method of claim 1, further comprising performing a transformation process to produce the mixed population.

4. The method of claim 3, further comprising, after performing the transformation process, adding a liquid medium including the selection agent to the mixed population to select the first mutant cells.

5. The method of claim 1, wherein the non-mutant cells comprise persister cells, the persister cells being metabolically inactive cells.

6. The method of claim 5, wherein enriching the first mutant cells relative to the persister cells comprises adding a cryoprotectant and then freezing and thawing the mixed population.

7. The method of claim 1, wherein the non-mutant cells comprise cells that spontaneously develop resistance to the selection agent but do not have the target DNA sequence.

8. The method of claim 7, wherein enriching the first mutant cells relative to the cells that spontaneously develop resistance to the selection agent but do not have the target DNA sequence comprises freezing and thawing the mixed population.

9. The method of claim 1, wherein the non-mutant cells comprise plasmid-based persister cells that carry a non-integrated plasmid comprising the selection marker and are resistant to the selection agent but that cannot increase in number.

10. The method of claim 9, wherein enriching the first mutant cells relative to the plasmid based-persister cells comprises diluting and outgrowing the mixed population cells.

11. The method of claim 1, wherein enriching the first mutant cells relative to the non-mutant cells in the mixed population comprises freezing and thawing the mixed population and wherein the freezing and thawing is performed after operations of post-transformation cell recovery and adding a liquid medium comprising the selection agent to the mixed population.

12. The method of claim 1, wherein enriching the first mutant cells relative to the non-mutant cells from the mixed population comprises freezing and thawing the mixed population and diluting and outgrowing the mixed population cells after thawing.

13. The method of claim 1, wherein removing the selection marker and counter-selection marker from cells of the population enriched for the first mutant cells comprises producing a second mixed population, the second mixed population comprising first mutant cells, second mutant cells having the target DNA sequence without the selection marker and counter-selection marker integrated into their genomes, and base strain cells.

14. The method of claim 13, further comprising isolating the cells of the second mixed population.

15. The method of claim 14, wherein isolating the cells of the second mixed population comprises optical identification of individual cells.

16. The method of claim 15, wherein isolating the cells further comprises single cell dispensing of the optically identified individual cells.

17. The method of claim 14, wherein isolating the cells comprises sorting with one or more of the group consisting of a viability stain, a fluorescent protein, and a reporting reagent.

18. The method of claim 1, further comprising isolating the cells of the enriched population through a limiting dilution process.

19. The method of claim 1, further comprising performing a limiting dilution of the enriched population into a plurality of wells containing a counter-selection agent such that substantially all of the wells contain no more than one cell that survives counter-selection.

20. The method of claim 1, wherein the cells are selected from:
bacterial cells and fungal cells.

21. The method of claim 1, wherein the cells are gram-negative bacterial cells.

22. A method comprising:
providing a mixed population of cells, the mixed population comprising first mutant cells and non-mutant cells, the first mutant cells having a target DNA sequence integrated on a left or right homology arm and a selection marker integrated into their genomes, the selection marker coding for resistance to a selection agent and the non-mutant cells comprising one or more of: (a) metabolically inactive cells, (b) cells that spontaneously develop resistance to the selection agent but do not have the target DNA sequence, and (c) cells that carry a non-integrated plasmid comprising the selection marker and are resistant to the selection agent but that cannot increase in number; and
in liquid, enriching the first mutant cells relative to the non-mutant cells in the mixed population to produce a homogenous population of the first mutant cells.

23. The method of claim 22, wherein the method is performed without generating clonal populations on a plate containing a solid growth medium and the selection agent.

24. The method of claim 22, wherein the non-mutant cells comprise cells that spontaneously develop resistance to the selection agent but do not have the target DNA sequence.

25. The method of claim 24, wherein enriching the first mutant cells relative to the cells that spontaneously develop resistance to the selection agent but do not have the target DNA sequence comprises freezing and thawing the mixed population.

26. The method of claim 22, wherein the non-mutant cells comprise cells that carry a non-integrated plasmid comprising the selection marker and are resistant to the selection agent but that cannot increase in number.

27. The method of claim 26, wherein enriching the first mutant cells relative to the non-mutant cells comprises diluting and outgrowing the mixed population cells.

28. The method of claim 22, wherein the non-mutant cells comprise metabolically inactive cells.

29. The method of claim 28, wherein enriching the first mutant cells relative to the non-mutant cells comprises freezing and thawing the mixed population in the presence of a cryoprotectant.

* * * * *